United States Patent [19]

Jackson

[11] 4,150,676
[45] Apr. 24, 1979

[54] ENDOTRACHEAL TUBES WITH INTUBATION DIRECTION CONTROL MEANS

[75] Inventor: Isaac S. Jackson, Greenwich, N.Y.

[73] Assignee: National Catheter Corp., Argyle, N.Y.

[21] Appl. No.: 592,226

[22] Filed: Jul. 1, 1975

[51] Int. Cl.² .................................... A61M 25/00
[52] U.S. Cl. .................... 128/351; 128/DIG. 9
[58] Field of Search .......... 128/348, 349 B, 349 BV, 128/351, DIG. 26, 350 R, DIG. 9, 2 M

[56] References Cited

U.S. PATENT DOCUMENTS

| 2,268,321 | 12/1941 | Flynn | 128/118 |
| 2,498,692 | 2/1950 | Mains | 128/242 |
| 3,470,876 | 10/1969 | Barchilon | 128/348 |
| 3,605,725 | 9/1971 | Bentov | 128/348 X |
| 3,605,750 | 9/1971 | Sheridan et al. | 128/348 |
| 3,776,222 | 12/1973 | Smiddy | 128/351 X |
| 3,810,474 | 5/1974 | Cross | 128/351 |
| 3,860,007 | 1/1975 | Binard et al. | 128/349 B |

FOREIGN PATENT DOCUMENTS 990417 6/1951 France ................................ 128/348

Primary Examiner—Dalton L. Truluck
Attorney, Agent, or Firm—Carroll F. Palmer

[57] ABSTRACT

Endotracheal tubes of the permanently curved, plastic, disposable type are improved for nasal intubation by intubation direction control means which comprises a pull-cord carried in a lumen formed in the tube wall along the inside of the curve in the tube.

2 Claims, 6 Drawing Figures

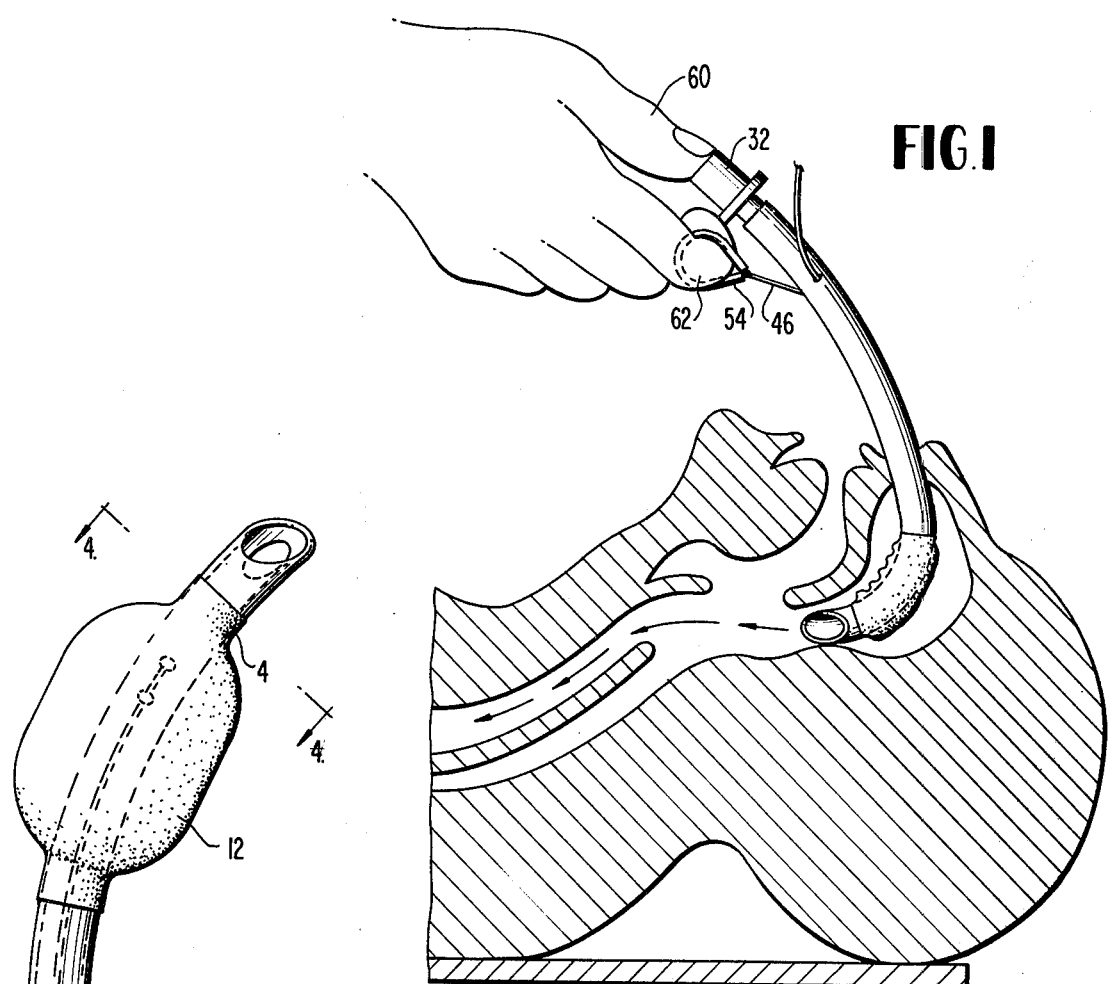
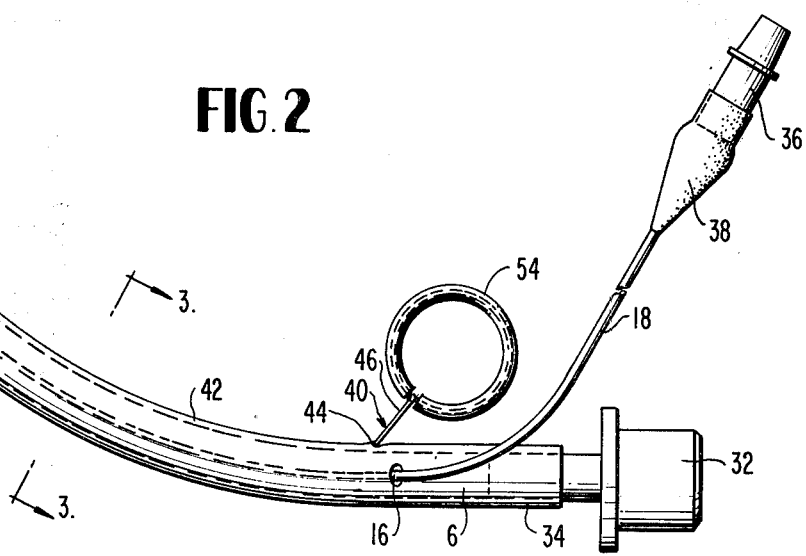
FIG.1
FIG.2

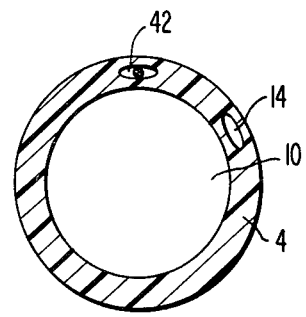
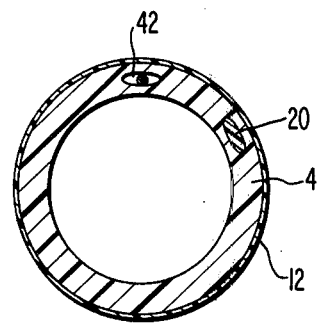
FIG.3  FIG.4
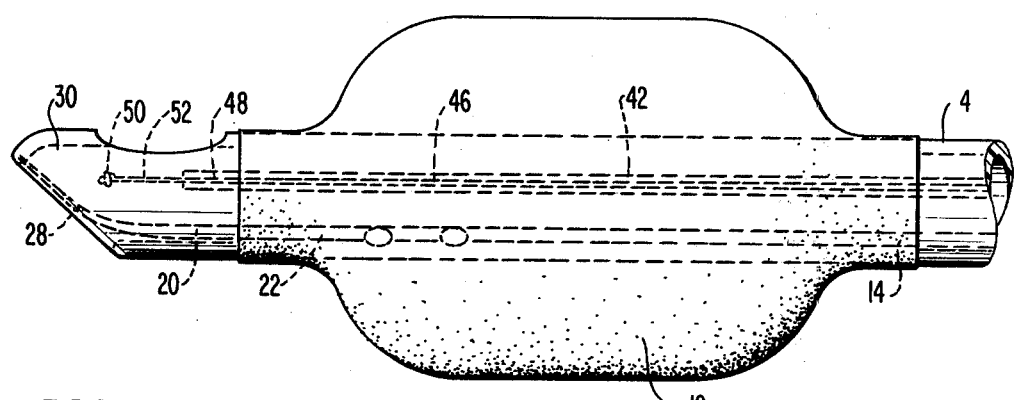
FIG.5
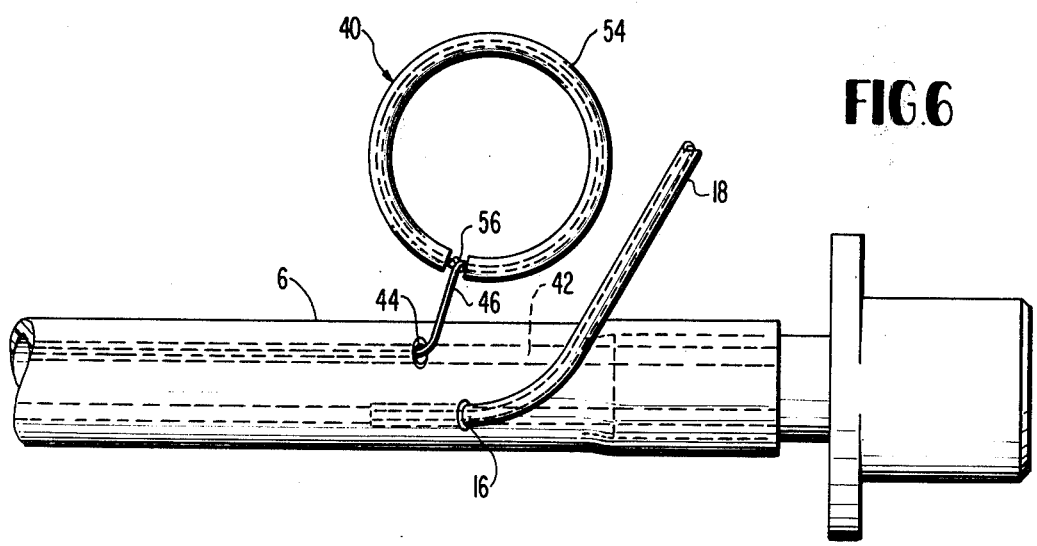
FIG.6

ENDOTRACHEAL TUBES WITH INTUBATION DIRECTION CONTROL MEANS

BACKGROUND OF THE INVENTION

1. Field of the Invention

This invention relates to endotracheal tubes of the permanently curved, plastic, disposable type. More particularly, it relates to such endo tubes designed to permit nasal intubation to be accomplished easily and without patient trauma.

2. Description of the Prior Art

Endotracheal tubes of the curved plastic disposable type have been commercially available for some years. At first such endo tubes were made with inflation tubes for balloon cuffs on the outside of the tubes or positioned within a single lumen in the tube. More recently improved endo tubes with unobstructed primary lumen having a secondary inflation lumen totally within the wall of the tube have been developed (see U.S. Pat. No. 3,615,793; 3,633,586; 3,725,522 and 3,755,525).

Nasal intubation with an endotracheal tube is a difficult procedure due to the anatomical configuration. The anesthesioligist must use a tube of proper size to fully supply the needs of the patient. This happens to be the largest tube the patient can pass. Human anatomy is such that the tube enters and advances until it reaches the back part of the nasal passage where the direction changes and the passage narrows. The tube tip invariably pokes into the back of the passage and resists turning the corner which leads toward the trachea. The tubes are curved and the anesthesioligist might use a lubricant, but neither of these insures easy passage.

Flexible metal probes or catheters have been provided with control cables for the purpose of guiding the probes or catheters around corners or bends in the body of a patient during installation of the probe or catheter (See U.S. Pat. No. 2,574,840). Intubating stylets have also been used to assist the curving of endotracheal tubes within the body of a patient during intubation (See U.S. Pat. Nos. 2,463,149 and 2,541,402).

Notwithstanding various improvements and developments in medico-surgical tubes, including endotracheal tubes, as mentioned above, there is a need to provide improvements in endotracheal tubes, particularly those used for nasal intubation, to permit easier and less traumatic introduction into the patient. Especially, there is a need for improved endotracheal tubes which will provide a maximum of bending control during intubation for advancing the tube around the corner at the back of the nasal passage in which this is accomplished without introducing detriments, e.g., partial blockage of the major lumen of the tube, destruction of full integrity of the major lumen of the tube or the like.

OBJECTS

A principal object of this invention is the provision of new endotracheal tubes of improved form.

A further object is the provision of endotracheal tubes having intubation direction control means which does not detrimentally affect operation of the endotracheal tubes or adversely affect any of the desired properties of such tubes.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by providing endotracheal tubes of the permanently curved, plastic, disposable type with intubation direction control means which comprises:

a lumen within the wall of said tube that extends along the inside of the curve in its central body portion, an opening into said lumen through the wall of said tube in the proximal end portion of said tube, a filament extending through said opening into and along said lumen to the distal end thereof, a weldment fixing the distal end of said filament to the distal end of said tube, and pull means of the proximal end of said filament external of said tube, said filament being movable in said lumen relative to said tube along its entire length proximal of said weldment whereby tension applied to said filament may produce bending of said tube greater than said normally curved condition.

Advantageously, the new endotracheal tubes are formed of plasticized vinyl chloride resin and the filament which constitutes a pull-cord for the control means is formed of nylon monofilament. The new endotracheal tubes also include further preferred features as will be apparent from the more detailed description given hereinafter.

BRIEF DESCRIPTION OF THE DRAWINGS

FIG. 1 is a diagrammatic view of a nasal intubation with an endotracheal tube of the invention.

FIG. 2 is a side elevational view of an endotracheal tube of the invention.

FIG. 3 is an enlarged sectional view taken on the line 3—3 of FIG. 2.

FIG. 4 is an enlarged sectional view taken on the line 4—4 of FIG. 2.

FIG. 5 is an enlarged, fragmentary side elevational view of the distal end portion of the endotracheal tube of FIG. 2.

FIG. 6 is an enlarged, fragmentary side elevational view of the proximal end portion of the endotracheal tube of FIG. 2.

DESCRIPTION OF PREFERRED EMBODIMENTS

Referring in detail to the drawings, the endotracheal tube 2 comprises a distal end portion 4, a proximal end portion 6 and a normally curved central body portion 8 which integrally joins the distal end portion to the proximal end portion. A primary lumen 10 comprises the major cross-sectional area of the tube.

A balloon cuff 12 is carried upon the distal end portion 4 and can be inflated through a secondary lumen 14 which extends within the wall of the tube 2 from the entrance 16 of the inflation tube 18 through the wall of the tube in the proximal end portion 6 to a plastic rod of x-ray opaque plastic material 20 which closes the distal end 22 of the secondary lumen 14. Within the region of the balloon cuff 12 there are provided two holes 24 and 26 through the side wall of the tube permitting fluid flow from the secondary lumen 14 to enter the balloon cuff for inflation thereof. The plastic rod 20 is fused to the plastic material of which the tube 2 is formed and provides an x-ray marking line 28 upon the distal end 30 of the tube.

The standard form of connector 32 is carried in the proximal end 34 of the endo tube and is used to attach gas delivery tubes and other equipment as is well known by those skilled in the use of endotracheal tubes. Also, the proximal end of the inflation tube 18 is provided with a check valve 36 and a pilot balloon 38. The endotracheal tubes are produced with a pre-formed normally curved form as shown in FIG. 2. The degree of curvature can be varied but generally it is a curve with a radius of about 14 cm.

Endotracheal tubes as described above are improved according to the present invention by providing them with the intubation direction control means 40. This comprises a tertiary lumen 42 within the wall of the tube and located so that the lumen extends along the inside curve in the tube. There is an opening 44 into said tertiary lumen 42 through the wall of the tube in the proximal end portion 6 and a filament 46 extends through the opening 44 into and along the tertiary lumen 42 to the distal end 48 thereof. A small knot 50 is tied in the end of the filament 46 and the plastic material of which the distal end 30 of the tube is formed is fused around the knot 50 and the adjacent portion of the filament 46 providing a weldment which fixes the distal end 52 of the filament to the distal end 30 of the tube. Pull means in the form of a ring 54 is provided on the proximal end of the filament external of the tube. Such pull means can be a short section of small diameter plastic tubing through which the filament 46 is threaded and then tied in a knot 56 to provide the ring—pull 54 on the end of the filament 46. The filament 46 can be twisted or braided thread but, advantageously, it is a monofilament of synthetic resin such as nylon monofilament.

When nasal intubation of a patient is attempted with an endotracheal tube, great difficulty may be encountered in getting the distal end of the tube to turn the corner of the nasal passage which leads towards the trachea. With the normal type of endo tubes, the normal procedure is to push upon the tube until there is sufficient yielding of the tube and the blocking tissues so that the tube will pass beyond this constriction and down into the trachea. In some cases, this can have a traumatic effect. As illustrated in FIG. 1, this problem is mitigated by the use of endotracheal tubes of the improved form of this invention. Procedure used is to insert the endotracheal tube until the tip reaches the back of the nasal passage. At this point, the thumb 60 of the operator is placed against the end of the connector 32 and the index finger 62 is put through the pull-ring 54. By pulling on the filament 46, the degree of curvature in the endotracheal tube can be increased and, if the tube is advanced at the same time, passage of the tube beyond this restricted area and down into the trachea can be accomplished without difficulty as illustrated in FIG. 1.

Although the intubation procedure as described above in connection with FIG. 1 is preferred for use with the new endotracheal tubes, alternative techniques can be employed. Thus, the degree and shape of curvature created in the endotracheal tube by tension applied to the control filament 46 will depend, to some extent, upon where the tube is held along its length by the anesthesioligist or other operator. If the tube is held by the central body portion near the distal end portion, the control filament is pulled, then only that portion of the tube above the hold point will change its curve. Accordingly, a very sharp curve can be imposed upon the end of the tube in this manner. On the other hand, if the tube is held by the central body portion toward the proximal end, then a smaller and more gradual degree of curvature is applied. Hence, selection of the position by which the endotracheal tube is held can be used to further control the degree and nature of curvature applied to the tube in the intubation operation. Upon full insertion of the tube into the trachea, release of tension on the control filament permits the tube to return to its normal preformed curvature which is designed to comply with the normal configuration of the trachea which, of course, serves to reduce trauma to the patient during surgical operation.

Although the primary use of endotubes of the invention is for nasal intubation, they may be effectively used for difficult oral intubations. This occurs with patients having unusual anatomy, arthritic patients where mobility of the neck is curtailed or patients with head and neck injuries that cause difficulties. Also, the intubation direction control means of the invention may be utilized on endotracheal tubes that do not include balloon cuffs.

A further advantage of the new form of endotracheal tubes of the invention is the fact that softer plastic material can be used in forming the tubes. This allows the tubes to conform more readily to the natural configuration of the trachea thereby further reducing the pressure points and mitigating trauma to the patient.

The embodiments of the invention in which an exclusive property or privilege is claimed are defined as follows:

1. In an endotracheal tube made of water-proof plastic material having a distal end portion, a proximal end portion, a normally curved central body portion integrally joining the distal end portion to the proximal end portion, a primary lumen comprising the major cross-sectional area of the tube, a balloon cuff carried upon the distal end portion, a secondary lumen within the wall of the tube and an inflation tube fixed to the proximal end of said secondary lumen for introduction of fluid therein, said secondary lumen discharging near its distal end into said balloon cuff for inflation thereof, the improvement which consists of intubation direction control means which comprises:
   a tertiary lumen within the wall of said tube that extends along the inside of the curve in said central body portion,
   an opening into said tertiary lumen through the wall of said tube in the proximal end portion of said tube,
   a filament extending through said opening into and along said tertiary lumen to the distal end thereof,
   a weldment fixing the distal end of said filament to the distal end of said tube, said filament being knotted at said weldment, and
   pull means on the proximal end of said filament external of said tube,
   said filament being moveable in said tertiary lumen relative to said tube along its entire length proximal of said weldment thereby tension applied to said filament may produce bending of said tube greater than said normally curved condition.

2. The endotracheal tube of claim 1 wherein said secondary lumen is positioned within the wall of said tube adjacent said tertiary lumen and the distal end of the secondary lumen is closed by a rod of x-ray opaque plastic which is fused to the plastic material of which said tube is formed.

* * * * *